United States Patent
Herron et al.

(10) Patent No.: US 7,816,016 B1
(45) Date of Patent: *Oct. 19, 2010

(54) ELECTROLUMINESCENT IRIDIUM COMPOUNDS AND DEVICES MADE THEREFROM

(75) Inventors: Norman Herron, Newark, DE (US); Mark A. Guidry, New Castle, DE (US); Viasceslav Petrov, Hockessin, DE (US); Nora Sabina Radu, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 537 days.

This patent is subject to a terminal disclaimer.

(21) Appl. No.: 11/315,741

(22) Filed: Dec. 22, 2005

Related U.S. Application Data

(63) Continuation-in-part of application No. 10/774,286, filed on Feb. 6, 2004, now Pat. No. 7,476,452, which is a continuation-in-part of application No. 10/768,298, filed on Jan. 30, 2004, now abandoned, and a continuation-in-part of application No. 10/366,295, filed on Feb. 13, 2003, now abandoned.

(60) Provisional application No. 60/640,813, filed on Dec. 29, 2004, provisional application No. 60/694,396, filed on Jun. 27, 2005.

(51) Int. Cl.
*H01L 51/00* (2006.01)
*C07D 213/02* (2006.01)
*C09K 11/06* (2006.01)
*H01L 51/54* (2006.01)

(52) U.S. Cl. .............. 428/690; 428/917; 313/504; 257/40; 257/E51.044; 546/4; 546/346

(58) Field of Classification Search .............. 546/4
See application file for complete search history.

(56) References Cited

U.S. PATENT DOCUMENTS

| | | | |
|---|---|---|---|
| 3,718,488 A | 2/1973 | Trofimenko et al. ......... 106/1.28 |
| 5,247,190 A | 9/1993 | Friend et al. .................. 257/40 |
| 5,408,109 A | 4/1995 | Heeger et al. ................. 257/40 |
| 5,552,678 A | 9/1996 | Tang et al. ................. 315/169.3 |
| 6,303,238 B1 | 10/2001 | Thompson et al. .......... 428/690 |
| 6,670,645 B2 | 12/2003 | Grushin et al. ................. 257/98 |
| 6,916,554 B2 | 7/2005 | Ma et al. ...................... 428/690 |
| 6,919,139 B2 | 7/2005 | Grushin et al. .............. 428/690 |
| 6,953,628 B2 | 10/2005 | Kamatani et al. ........... 428/690 |
| 7,011,897 B2 | 3/2006 | Thompson et al. .......... 428/690 |
| 7,198,730 B2 * | 4/2007 | Herron et al. .......... 252/301.16 |
| 7,320,835 B2 * | 1/2008 | Herron ....................... 428/690 |
| 7,476,452 B2 * | 1/2009 | Dobbs et al. ................ 428/690 |
| 2001/0019782 A1 | 9/2001 | Igarashi et al. .............. 428/690 |
| 2001/0053462 A1 | 12/2001 | Mishima ..................... 428/690 |
| 2002/0064681 A1 | 5/2002 | Takiguchi et al. ........... 428/690 |
| 2002/0134984 A1 | 9/2002 | Igarashi ........................ 257/79 |
| 2002/0182441 A1 | 12/2002 | Lamansky et al. .......... 428/690 |
| 2003/0124381 A1 | 7/2003 | Thompson et al. .......... 428/690 |
| 2003/0197183 A1 | 10/2003 | Grushin et al. ................. 257/79 |
| 2004/0197602 A1 | 10/2004 | Dobbs et al. ................ 428/690 |
| 2005/0037233 A1 | 2/2005 | Dobbs et al. ................ 428/690 |
| 2005/0048312 A1 | 3/2005 | Herron et al. ............... 428/690 |

FOREIGN PATENT DOCUMENTS

| | | |
|---|---|---|
| EP | 0 433 861 | 7/1994 |
| EP | 1 191 614 A2 | 3/2002 |
| EP | 1 175 128 A2 | 1/2003 |
| WO | WO 96/03410 A1 | 2/1996 |

(Continued)

OTHER PUBLICATIONS

Boere, R.T. et al., "Complexes of Hybrid Ligands. Synthesis of a Fluoro-Alcohol Diarylphosphino Ligand and Its Complexes with Pt2+, Pd2+, Ni2+, Co2+,Cu+, and Rh3: Crystal and Molecular Structure of a Trans Square-Planar Ni2+ Complex with Two Bidentate Ligands Showing Cis-Trans Isomerism in Solution", *Inorg. Chem.*, 1985, 24, 3680-3687.

(Continued)

*Primary Examiner*—Marie R. Yamnitzky
(74) *Attorney, Agent, or Firm*—Woodcock Washburn LLP

(57) ABSTRACT

Provided are complexes of the formula:

(I)

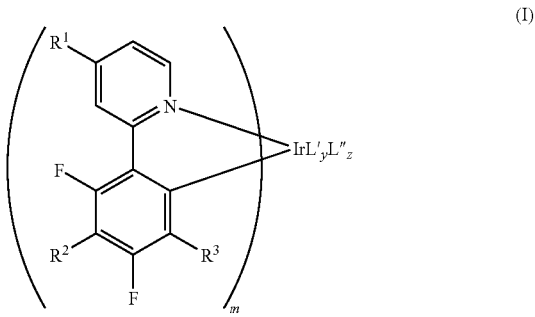

where $R^1$ is H, $R^4$, $OR^4$, $N(R^4)_2$ or $CHAr_2$; $R^2$ is H, $C_nF_{2n+1}$, $C_nF_{2n+1}SO_2$, $COOR^4$, or CN; $R^3$ is H, $C_nF_{2n+1}$, $C_nF_{2n+1}SO_2$, $COOR^4$, or CN; $R^4$ is the same or different at each occurrence and is H, alkyl, or aryl, or adjacent $R^4$ groups can join together to form a 5- or 6-membered ring, or adjacent $R^4$ groups can join together to form a 5- or 6-membered ring; or adjacent $R^4$ groups can join together to form a multicyclic moiety; each Ar is independently an aryl group; L' is a polydentate ligand that is not a phenylpyridine, phenylpyrimidine, or phenylquinoline; L" is a monodentate ligand, and is not a phenylpyridine, and phenylpyrimidine, or phenylquinoline; m is 1, 2 or 3; n is an integer from 1 through 20; y is 0, 1 or 2; and z is 0 or an integer from 1 through 4; with the proviso that the compound is charge neutral and the iridium is hexacoordinate.

15 Claims, 1 Drawing Sheet

FOREIGN PATENT DOCUMENTS

| | | |
|---|---|---|
| WO | WO 00/57676 A1 | 9/2000 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/44189 A1 | 6/2002 |
| WO | WO 03/040257 | 5/2003 |
| WO | WO 03/063555 | 7/2003 |
| WO | WO 03/069961 A1 | 8/2003 |
| WO | WO 03/084972 A1 | 10/2003 |

OTHER PUBLICATIONS

O'Brien, D.F. et al., "Electrophosphoresence from a Doped Polymer Light Emitting Diode", *Synthetic Metals*, 2001, 116(1-3), 379-383.

Campbell, I.H. et al., "Excitation Transfer Processes in a Phosphor-Doped Poly(*p*-Phenylene Vinylene) Light-Emitting Diode", *Physical Review B.*, 65, 085210-1-085210-8, (2002).

Gustafsson, G., Flexible Light-Emitting Diodes made from Soluble Conducting Polymer, *Nature*, 1992, 357, 477-479.

Kurykin, M.A. et al., "Reaction of Trans-Perfluoro-2-Pentene with Ammonia", Izvestiya Akademii Nauk SSSR, *USSR. Ser. Khim*, 1980, 2827-2829, English language abstract attached.

Grushin, V.V. et al., "Facile Preparation and Synthetic Applications of LiCH2C(CF3)2OLi", *Journal of Fluorine Chemistry*, 2002, 117, 121-129.

Othmer, K., *Encyclopedia of Chemical Technology*, 1996, 18, 4$^{th}$ ed., 837-860.

Baldo, M.A. et al., "Very High-Efficiency Green Organic Light-Emitting Devices Based on Electrophosphorescence", *Applied Physics Letters*, 1999, 75(1), 4-6.

Markus, J, *Electronics and Nucleonics Dictionary*, 1966, 3$^{rd}$ edition, 470 and 476.

Djurovich, P.I et al., Ir(III) Cyclometalated Complexes as Efficient Phosphorescent Emitters in Polymer Blend and Organic LEDs, *Polymer Preprints*, 2000, 41(1), 770-771.

Chatani, N. et al., "Ru3(CO) 12-Catalyzed Reaction of Pyridyibenzenes with Carbon Monoxide and Olefins. Carbonylation at a C-H Bond in the Benzene Ring", *J. Org. Chem.*, 1997, 62, 2604-2610.

Gosmini, C. et al., "Electrosynthesis of Functionalized 2-arylpyridines from Functionalized Aryl and Pyridine Hatides Catalyzed by Nickel Bromide 2.2'-Bipyridine Complex", *Tetrahedron Letters*, 2000, 41, 5039-5042.

Cacchi, S. et al., "The Palladium-Catalyzed Transfer Hydrogenation/ Heterocyclization of B-(2-Aminophenyl-a-B-ynones. An Approach to 2-Aryl-and 2-vinytquinolines", *Synlett*, 1999, 4, 401-404.

Baldo, M.A. et al., "High-Efficiency Fluorescent Organic Light-Emitting Devices using a Phosphorescent Sensitizer", *Nature*, 2000, 403, 750-753.

Baldo, M.A. et al., "Highly Efficient Phosphorescent Emission from Organic Electroluminescent Devices", *Nature*, 1998, 395, 151-154.

Wang, Y. et al., "(Hydroxyphenyl) Pyridine Derivative, its Metal Complexes and Application as Electroluminescence Material", *Chemical Abstracts Service*, 2000, Database No. 133-315395.

Dedeian, K. et al., "A New Synthetic Route to the Preparation of a Series of Strong Photoreducing Agents: fac tris-Ortho-Metalated Complexes of Iridium (III) with Substituted 2-Phenylpyridines", *Inorg. Chem.*, 1991, 30(8), 1685-1687.

Lamansky, S. et al., "Highly Phosphorescent Bis-Cyclometalated Iridium Complexes: Synthesis Photophysical Characterization and Use in Organic Light Emitting Devices", *J. Am. Chem Soc.*, 2001, 123, 4304-4312.

Lamansky, S. et al., "Synthesis and Characterization of Phosphorescent Cyclometalated Iridium Complexes", *Inorg Chem.*, 2001, 40, 1704-1711.

Lamansky, S. et al., "Molecularly Doped Polymer Light-Emitting Diodes Utilizing Phosphorescent Pt(II) and Ir (III) Dopants", *Organic Electronics*, 2001, 2, 53-62.

Thompson, et al., "Ir(III) Cyclometalated Complexes as Efficient Phosphorescent Emitters in Polymer Blend Organic LEDs", *Polymer Preprints*, 2000, 41(1), 770-771.

Lohse, O. et al., "The Palladium Catalysed Suzuki Coupling of 2-and4- Chloropyridines", Synlett, 1999, 1, 45-48.

\* cited by examiner

ELECTROLUMINESCENT IRIDIUM COMPOUNDS AND DEVICES MADE THEREFROM

CROSS REFERENCE

This application is a Continuation-in-Part of U.S. Ser. No. 10/774,286, filed Feb. 6, 2004, now U.S. Pat. No. 7,476,452, which is a Continuation-in-Part of U.S. Ser. No. 10/768,298, filed Jan. 30, 2004 (now abandoned) and a Continuation-in-Part of U.S. Ser. No. 10/366,295, filed Feb. 13, 2003 (now abandoned), the disclosures of each are incorporated by reference herein. This application also claims benefit to U.S. Application No. 60/640,813, filed Dec. 29, 2004 and U.S. Application No. 60/694,396, filed Jun. 27, 2005, the disclosure of each is incorporated by reference in their entireties.

FIELD

This disclosure relates generally to a transition metal complexes and their use in electronic devices.

BACKGROUND INFORMATION

Organic electronic devices convert electrical energy into radiation, detect signals through electronic processes, convert radiation into electrical energy, or include one or more organic semiconductor layers. Most organic electronic devices include a conductive layer (such as a light-emitting or photoactive layer) positioned between two electrodes. In some devices, a charge transport layer can be utilized between the conductive layer and an electrode. For example, a hole transport layer can be positioned between the conductive layer and the anode and a electron transport layer can be positioned between the conductive layer and the cathode.

Thus, what is needed are new materials for use in electronic devices.

SUMMARY

There is provided iridium complexes (generally referred as "Ir(III) compounds") having Formula I:

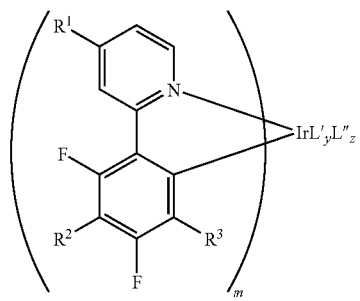

(I)

wherein:

$R^1$ is H, $R^4$, $OR^4$, $N(R^4)_2$ or $CHAr_2$;

$R^2$ is H, $C_nF_{2n+1}$, $C_nF_{2n+1}SO_2$, $COOR^4$, or CN;

$R^3$ is H, $C_nF_{2n+1}$, $C_nF_{2n+1}SO_2$, $COOR^4$, or CN;

$R^4$ is the same or different at each occurrence and is H, alkyl, or aryl, or adjacent $R^4$ groups can join together to form a 5- or 6-membered ring; or adjacent $R^4$ groups can join together to form a multicyclic moiety;

each Ar is independently an aryl group;

L' is a polydentate ligand that is not a phenylpyridine, phenylpyrimidine, or phenylquinoline;

L" is a monodentate ligand, and is not a phenylpyridine, and phenylpyrimidine, or phenylquinoline;

n is an integer from 1 through 20;

y is 0, 1 or 2; and z is 0 or an integer from 1 through 4, with the proviso that the compound is charge neutral and the iridium is hexacoordinate.

In one embodiment, there is provided substituted 2-phenylpyridine precursor compounds from which the above Ir(III) compounds are can be made. These compounds have a Formula II below:

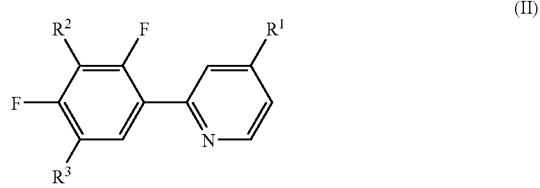

(II)

where $R^1$, $R^2$, and $R^3$ are as defined in Formula I above.

It is understood that there is free rotation about the phenylpyridine bond. However, for the discussion herein, the compounds will be described in terms of one orientation.

In one embodiment, there is provided an organic electronic device having at least one layer comprising at least one complex described herein. In yet another embodiment, there is provided an organic electronic device having at least one active layer composition comprising at least one complex of Formula (I).

The foregoing general description and the following detailed description are exemplary and explanatory only and are not restrictive of the invention, as defined in the appended claims.

DESCRIPTION OF THE DRAWINGS

Embodiments are illustrated in the accompanying figures to improve understanding of concepts as presented herein.

Figure 1:
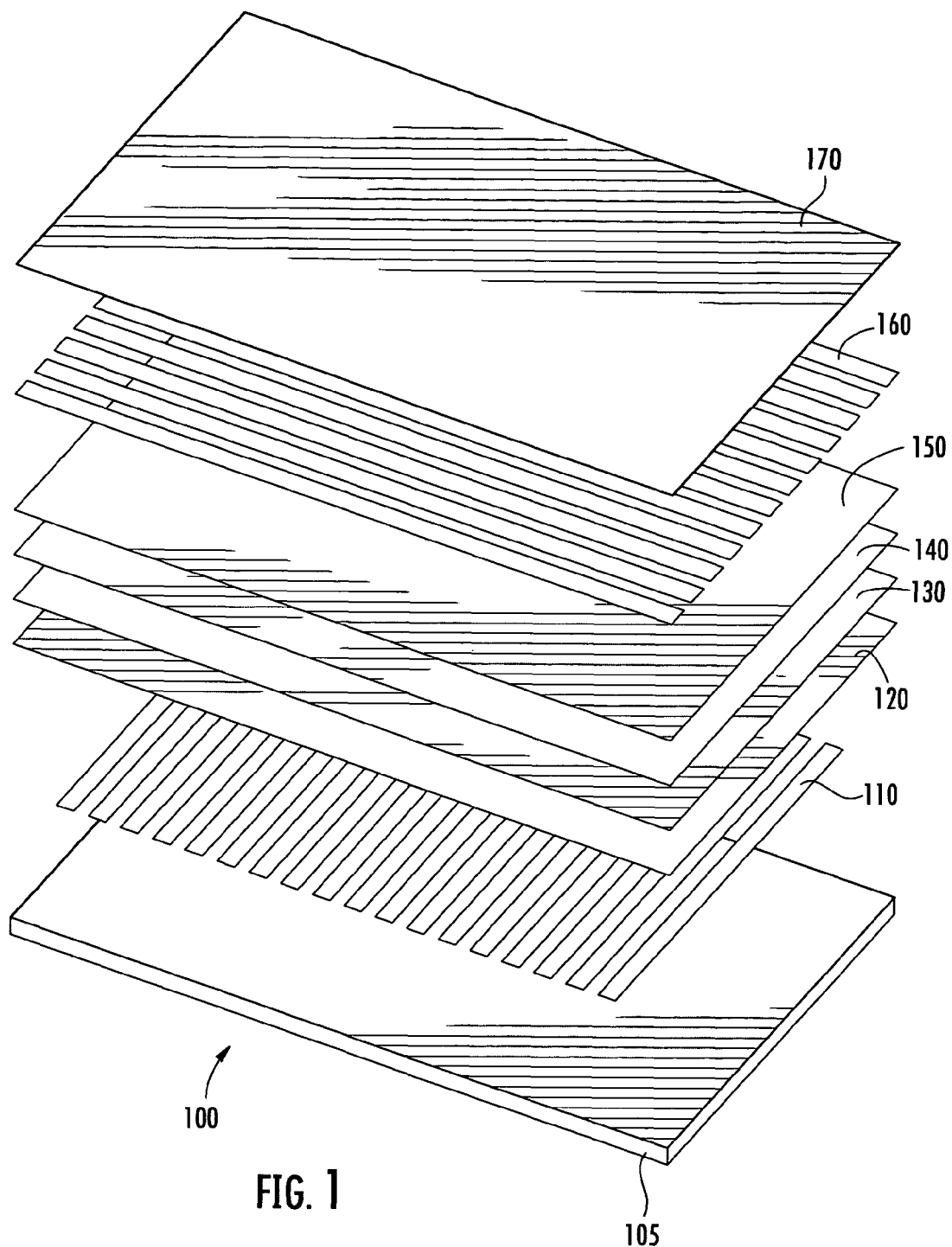
FIG. 1 is a schematic diagram of one illustrative example of a light-emitting device (LED).

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Organic electronic devices that emit light, such as light-emitting diodes that make up displays, are present in many different kinds of electronic equipment. In such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

Compounds having Formula I, as described herein, are useful as emitters, as hosts for other emitters, as charge transport materials, as charge blocking and as electron transport materials. In one embodiment, the compounds are useful as blue emitters.

In one embodiment of Formula I, $R^1$ is $N(R^4)_2$ or $CHAr_2$.

In one embodiment, $R^1$ is $N(R^4)_2$. As discussed above, adjacent $R^4$ groups of a $N(R^4)_2$ group join together to form a 5- or 6-membered ring. Examples of such rings include pyrrole, azole, oxazole, and pyridinyl. In one embodiment, $N(R^4)_2$ is a nitrogen-containing multicyclic moiety. As used herein, the term "nitrogen-containing multicyclic moiety" refers to a moiety that comprises at least two rings where one of the rings includes the nitrogen atom of the $N(R^4)_2$ group. In one embodiment, the moiety has two or three rings. In one embodiment, at least one of the rings is aromatic. In yet other embodiments, all rings are aromatic in character. Examples of these multicyclic moieties include indole, indoline, carbazole, tetrahydrocarbazole, phenanthroline, phenazine, phenanthridine, quinoxaline and the like.

In one embodiment of Formula I, $R^1$ is $CHAr_2$. Ar can be the same or different and can be any aryl group. Ar can be polycyclic. The Ar group can be unsubstituted or substituted with alkyl, aryl, halide, carboxyl, sulfoxyl, or amino groups. In one embodiment, Ar is an aryl group having from 6 to 30 carbon atoms. In one embodiment, Ar is a heteroaryl group having 2-30 carbon atoms. In one embodiment, both Ar are phenyl groups. In one embodiment, both Ar are phenyl groups having at least one alkyl substituent having 1-20 carbon atoms.

In one embodiment of Formula I, $R^2$ and $R^3$ are independently selected from H, $CF_3$, $C_2F_5$, n-$C_3F_7$, i-$C_3F_7$, $C_4F_9$, $CF_3SO_2$, COOR' and CN. In one embodiment, R' can be a substituted or unsubstituted alkyl.

In one embodiment, where $R^1$ is a N-heteroring (carbazolyl, for example), diarylamino (such as diphenylamine where one or both phenyls are optionally substituted with p-carbazole), or diarylmethyl, the compounds are useful as hole transport materials.

In one embodiment, where $R^1$ is an azole (such as oxadiazole), phenazine, phenanthroline, or quinoxaline, the compounds are useful as electron transport materials.

In one embodiment of Formula I, L' ligand is a monoanionic bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

The β-enolate ligands generally have the Formula III

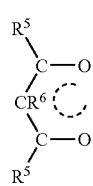

(III)

where $R^5$ is the same or different at each occurrence. The $R^5$ groups can be hydrogen, halogen, substituted or unsubstituted alkyl, aryl, alkylaryl or heterocyclic groups. The $R^6$ group can be hydrogen, halogen, substituted or unsubstituted alkyl, aryl, alkylaryl or heterocyclic groups. Adjacent $R^5$ and $R^6$ groups can be joined to form five- and six-membered rings, which can be substituted. In one embodiment, $R^5$ groups are selected from $C_n(H+F)_{2n+1}$, $C_6H_5$, c-$C_4H_3S$, and c-$C_4H_3O$, where n is an integer from 1 through 20. The $R^6$ group can be H, substituted or unsubstituted alkyl, aryl, alkylaryl, heterocyclic groups or fluorine.

Examples of suitable β-enolate ligands include the compounds listed below. The abbreviation for the β-enolate form is given below in brackets.
2,4-pentanedionate [acac]
1,3-diphenyl-1,3-propanedionate [DI]
2,2,6,6-tetramethyl-3,5-heptanedionate [TMH]
4,4,4-trifluoro-1-(2-thienyl)-1,3-butanedionate [TTFA]
7,7-dimethyl-1,1,1,2,2,3,3-heptafluoro-4,6-octanedionate [FOD]
1,1,1,3,5,5,5-heptafluoro-2,4-pentanedionate [F7acac]
1,1,1,5,5,5-hexafluoro-2,4-pentanedionate [F6acac]
1-phenyl-3-methyl-4-1-butyryl-pyrazolinonate [FMBP]

The β-dicarbonyl parent compounds, are generally available commercially. The parent compound 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step according to the procedure published in *Izv. AN USSR. Ser. Khim.* 1980, 2827. This compound should be stored and reacted under anhydrous conditions as it is susceptible to hydrolysis.

The hydroxyquinolinate ligands can be substituted with groups such as alkyl or alkoxy groups which may be partially or fully fluorinated. Examples of suitable hydroxyquinolinate ligands include (with abbreviation provided in brackets):
8-hydroxyquinolinate [8hq]
2-methyl-8-hydroxyquinolinate [Me-8hq]
10-hydroxybenzoquinolinate [10-hbq]

The parent hydroxyquinoline compounds are generally available commercially.

Phosphino alkoxide ligands generally have Formula IV:

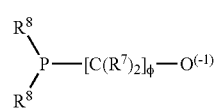

(IV)

where
$R^7$ can be the same or different at each occurrence and is selected from H and $C_n(H+F)_{2n+1}$,
$R^8$ can be the same or different at each occurrence and is selected from $C_n(H+F)_{2n+1}$ and $C_6(H+F)_5$, or $C_6H_{5-b}(R^9)_b$,
$R^9$ is $CF_3$, $C_2F_5$, n-$C_3F_7$, i-$C_3F_7$, $C_4F_9$, or $CF_3SO_2$,
φ is 2 or 3;
b is 0 or an integer from 1 through 5; and
n is an integer from 1 through 20.

Examples of suitable phosphino alkoxide ligands include (with abbreviation provided in brackets):
3-(diphenylphosphino)-1-oxypropane [dppO], and 1,1-bis(trifluoromethyl)-2-(diphenylphosphino)-ethoxide[tfmdpeO].

Some of the parent phosphino alkanol compounds are available commercially, or can be prepared using known procedures, such as, for example, the procedure reported in *Inorg. Chem.* 1985, v. 24, p. 3680 or in *J. Fluorine Chem.* 2002, 117, 121.

In one embodiment, L' is a ligand coordinated through a carbon atom which is part of an aromatic group. The ligand can have Formula V:

Ar[—(CH$_2$)$_q$—Y]$_p$  (V)

wherein Ar is an aryl or heteroaryl group, Y is a group having a heteroatom capable of coordinating to Ir, q is 0 or an integer from 1 through 20, p is an integer from 1 through 5, and further wherein one or more of the carbons in (CH$_2$)$_q$ can be replaced with a heteroatom and one or more of the hydrogens in (CH$_2$)$_q$ can be replaced with D or F. In one embodiment, Y is selected from N(R$^{10}$)$_2$, OR$^{10}$, SR$^{10}$, and P(R$^{11}$)$_2$, wherein R$^{10}$ is the same or different at each occurrence and is H, C$_n$H$_{2n+1}$ or C$_n$(H+F)$_{2n+1}$ and R$^{11}$ is the same or different at each occurrence and is selected from R$^{10}$, Ar and substituted Ar.

In one embodiment, Ar is phenyl, q is 1, Y is P(Ar)$_2$, and p is 1 or 2.

Monodentate ligand L" can be anionic or nonionic. Anionic ligands include, but are not limited to, H$^-$ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L', such as O-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L" ligand can be a non-ionic ligand, such as CO or a monodentate phosphine ligand. The phosphine ligands can have Formula VI

P(R$^{11}$)$_3$  (VI)

where R$^{11}$ is an alkyl group or Ar. The alkyl group can have heteroatoms, and can have from 1 to 20 carbon atoms. Ar represents an aryl or heteroaryl group. R$^{11}$ can be unsubstituted or substituted with alkyl, heteroalkyl, aryl, heteroaryl, halide, carboxyl, sulfoxyl, or amino groups. The phosphine ligands are generally available commercially.

In one embodiment of Formula I, the compound is tris-cyclometallated, where m is 3 and y and z are 0. The compound can be facial, meridional, or a combination of isomers.

In one embodiment of Formula I, m is 2. In one embodiment, y is 1 and z is 0.

In one embodiment of Formula I, m is 1. In one embodiment, y is 1 and z is 2. In one embodiment at least one L" ligand is a hydride. In one embodiment L' is a ligand coordinated through a carbon atom which is part of an aromatic group.

In one embodiment, the compounds having Formula I exhibit blue luminescence. In one embodiment, the compounds have photoluminescent and/or electroluminescent spectra which have a maximum at about 500 nm or less. In one embodiment, the maximum is less than about 480 nm.

Examples of iridium compounds having Formula I are given in Table 1 below.

TABLE 1

Compounds of Formula I where z is 0

| Complex | R$^1$ | R$^2$ | R$^3$ | m | L' | y |
|---------|-------|-------|-------|---|----|----|
| 1-a | H | H | H | 3 | — | 0 |
| 1-b | H | CF$_3$ | H | 3 | — | 0 |
| 1-c | H | COOMe | H | 3 | — | 0 |
| 1-d | H | CN | H | 3 | — | 0 |
| 1-e | CH$_3$ | H | H | 3 | — | 0 |
| 1-f | CH$_3$ | CF$_3$ | H | 3 | — | 0 |
| 1-g | CH$_3$ | COOMe | H | 3 | — | 0 |
| 1-h | CH$_3$ | CN | H | 3 | — | 0 |
| 1-i | CH$_3$ | H | H | 2 | PO | 1 |
| 1-j | t-butyl | H | H | 3 | — | 0 |
| 1-k | OMe | CF$_3$ | H | 3 | — | 0 |
| 1-l | OMe | COOMe | H | 3 | — | 0 |
| 1-m | OMe | CN | H | 3 | — | 0 |
| 1-n | OMe | CF$_3$ | CF$_3$ | 3 | — | 0 |
| 1-o | NMe$_2$ | H | H | 3 | — | 0 |
| 1-p | NMe$_2$ | CF$_3$ | H | 3 | — | 0 |
| 1-q | NMe$_2$ | COOMe | H | 3 | — | 0 |
| 1-r | NMe$_2$ | CN | H | 3 | — | 0 |
| 1-s | NMe$_2$ | CF$_3$SO$_2$ | H | 3 | — | 0 |
| 1-t | NMe$_2$ | C$_2$F$_5$ | H | 3 | — | 0 |
| 1-u | NMe$_2$ | CF(CF$_3$)$_2$ | H | 3 | — | 0 |
| 1-v | NMe$_2$ | H | H | 2 | PO | 1 |
| 1-w | NPh$_2$ | CF$_3$ | H | 3 | — | 0 |
| 1-x | NPh$_2$ | COOMe | H | 3 | — | 0 |
| 1-y | NPh$_2$ | CN | H | 3 | — | 0 | where "PO" represents the bidentate monoanionic ligand having Formula VII:

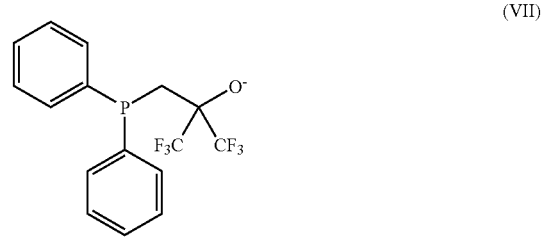

(VII)

In one embodiment of Formula I, the complex comprises a ligand derived from ligand precursors having Formula VIII, Formula IX, Formula X, Formula XI, and Formula XII below:

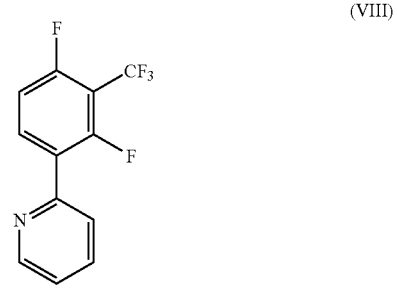

(VIII)

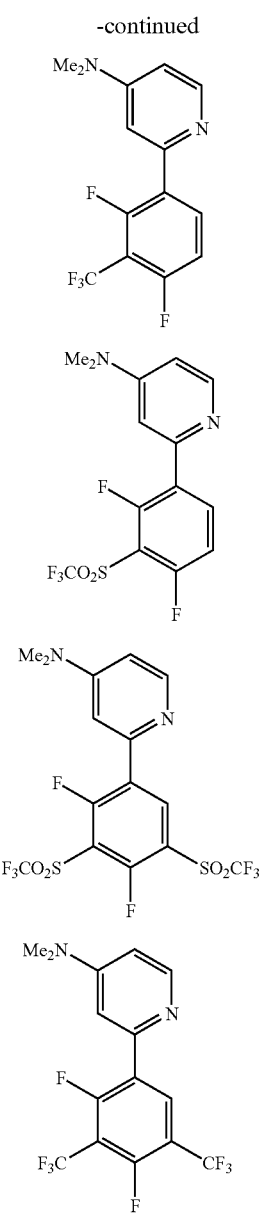

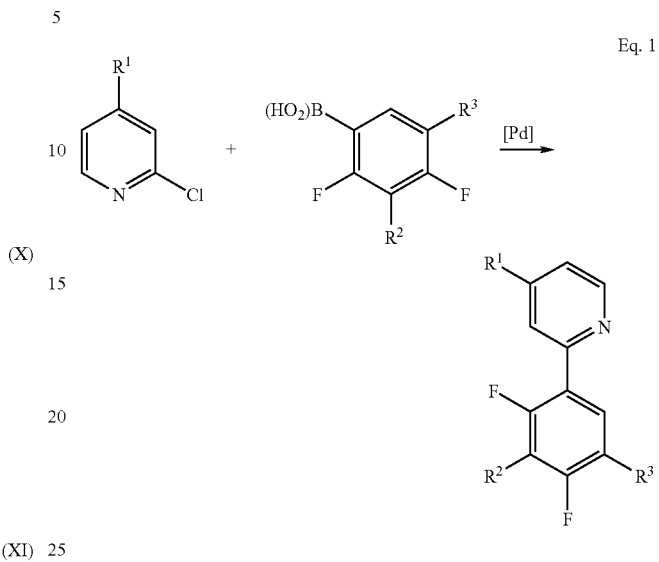

with arylboronic acid as described in O. Lohse, P. Thevenin, E. Waldvogel *Synlett*, 1999, 45-48. This reaction is illustrated in Equation (1) below:

Examples of 2-phenylpyridine compounds include Formulae VIII through XII, shown above.

The 2-phenylpyridines thus prepared are used for the synthesis of the cyclometalated iridium compounds. A convenient one-step method has been developed employing commercially available iridium trichloride hydrate and silver trifluoroacetate. The reactions are generally carried out with an excess of 2-phenylpyridine, phenylpyrimidine, phenylisoquinoline or phenylquinoline, without a solvent, in the presence of 3 equivalents of $AgOCOCF_3$. This reaction is illustrated in Equation (2) below:

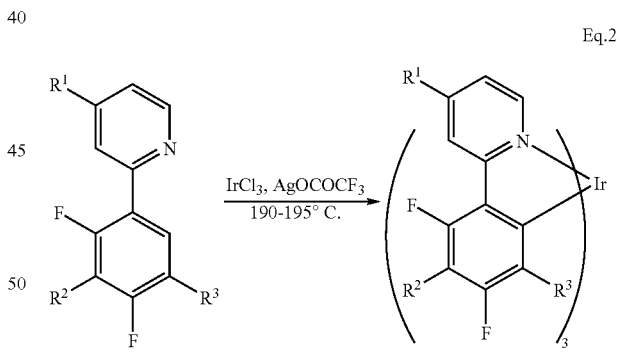

Tris-cyclometalated iridium compounds having Formula I where m is 3, can be isolated, purified, and fully characterized by elemental analysis, $^1H$ and $^{19}F$ NMR spectral data, and, for some compounds, single crystal X-ray diffraction. In some cases, mixtures of isomers are obtained. Often the mixture can be used without isolating the individual isomers.

Bis-cyclometalated iridium compounds having Formula I where m is 2, may, in some cases, be isolated from the reaction mixture using the same synthetic procedures as preparing the tris-cyclometalated compounds above. The compounds can also be prepared by first preparing an intermediate iridium dimer The Ir(III) compounds are neutral and non-ionic, and can be sublimed intact. Thin films of these materials obtained via vacuum deposition exhibit good to excellent electroluminescent properties. Introduction of fluorine substituents into the ligands on the iridium atom increases both the stability and volatility of the compounds. As a result, vacuum deposition can be carried out at lower temperatures and decomposition of the compounds can be avoided. Introduction of fluorine substituents into the ligands can often reduce the non-radiative decay rate and the self-quenching phenomenon in the solid state. These reductions can lead to enhanced luminescence efficiency.

The iridium compounds described herein are generally prepared from the appropriate substituted 2-phenylpyridine compound. The substituted 2-phenylpyridines, as shown in Formula II above, are prepared, in good to excellent yield, using the Suzuki coupling of the substituted 2-chloropyridine

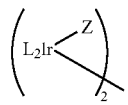

where L is the same or different and is a phenylpyridine ligand, and Z is Cl or $OR^{12}$, where $R^{12}$ is H, $CH_3$, or $C_2H_5$. The iridium dimers can generally be prepared by first reacting iridium trichloride hydrate with the 2-phenylpyridine and optionally adding $NaOR^{12}$.

Mono-cyclometalated iridium compounds can, in some cases, be isolated from reaction mixtures formed by the above-described processes. Such mono-cyclometallated species can be favored by use of phosphine containing ligands such as that shown in formula VII and by using a stoichiometric excess of such ligands (>2 equivalents per Ir) and 1 equivalent of the appropriate cyclometallating phenylpyridine, phenylpyrimidine, phenylquinoline, or phenylisoquinoline. These materials can be isolated from the reaction mixture by standard techniques, such as chromatography on silica with methylene chloride eluent.

In one embodiment, at least one compound of Formula I is a component of a composition. The composition may be in any form, including but not limited to, solvents, processing aids, other charge emitting or blocking materials, and such compounds may be in the form of a solvent, emulsion, colloidal dispersion, etc.

Device

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer*, Nature 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4$^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino)styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

The iridium compounds described herein are particularly useful as the photoactive material in layer 130, or as electron transport material in layer 140. In one embodiment, the iridium compounds described herein are used as the light-emitting material in diodes. Additional materials can be present in the emitting layer with the iridium compound.

In some cases the iridium compounds may be present in more than one isomeric form, or mixtures of different compounds may be present. It will be understood that in the discussion of OLEDs, the term "the iridium compound" is intended to encompass mixtures of compounds and/or isomers.

In addition to the iridium compounds, any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used.

Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or bandgap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

The iridium compounds described herein often are phosphorescent and photoluminescent and may be useful in applications other than OLEDs. For example, organometallic compounds of iridium have been used as oxygen sensitive indicators, as phosphorescent indicators in bioassays, and as catalysts. The bis cyclometalated compounds can be used to synthesize tris cyclometalated compounds where the third ligand is the same or different.

DEFINITIONS

As used herein, the term "multicyclic moiety" refers to a moiety that comprises at least two rings, which can be joined by a single bond or fused together. The rings can be alicyclic or aromatic.

The term "p-carbazole" refers to a carbazole substitutent which is attached via the nitrogen.

The term "monomer" refers to a compound capable of being polymerized. The term "monomeric unit" refers to units which are repeated in a polymer.

The term "polymeric" is intended to encompass oligomeric species and include materials having 2 or more monomeric units.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, where "a" and "b" represent different coordinating atoms, having octahedral geometry, in which the three "a" atoms are all adjacent, i.e. at the corners of one face of the octahedron. The term "meridional" is intended to mean one isomer of a complex, $Ma_3b_3$, having octahedral geometry, in which the three "a" atoms occupy three positions such that two are trans to each other. The term "hexacoordinate" is intended to mean that six groups or points of attachment are coordinated to a central metal. The phrase "adjacent to," when used to refer to layers in a device, does not necessarily mean that one layer is immediately next to another layer. On the other hand, the phrase "adjacent R groups," is used to refer to R groups that are next to each other in a chemical formula (I.e., R groups that are on atoms joined by a bond). The term "photoactive" refers to any material that exhibits electroluminescence and/or photosensitivity. In the Formulae and Equations, the letters L, R, Y, and Z are used to designate atoms or groups which are defined within. All other letters are used to designate conventional atomic symbols. The term "(H+F)" is intended to mean all combinations of hydrogen and fluorine, including completely hydrogenated, partially fluorinated or perfluorinated substituents.

The term "aryl" includes heteroaryl groups having at least one heteroatom. The term "alkyl" includes heteroalkyl groups having at least one heteroatom. In one embodiment, the heteroatom is O, S, or N.

The use of "a" or "an" are employed to describe elements and components of the invention. This is done merely for convenience and to give a general sense of the invention. This description should be read to include one or at least one and the singular also includes the plural unless it is obvious that it is meant otherwise.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector).

As used herein, the term "charge transport," when referring to a layer or material is intended to mean such layer or material facilitates migration of such charge through the thickness of such layer, material, member, or structure with relative efficiency and small loss of charge, and is meant to be broad enough to include materials that may act as a hole transport or an electron transport material. The term "electron transport" when referring to a layer or material means such a layer or material, member or structure that promotes or facilitates migration of electrons through such a layer or material into another layer, material, member or structure. The term "charge-blocking," when referring to a layer, material, member, or structure, is intended to mean such layer, material, member or structure reduces the likelihood that a charge migrates into another layer, material, member or structure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

EXAMPLES

The concepts described herein will be further described in the following examples, which do not limit the scope of the invention described in the claims.

All percentages are by weight, unless otherwise indicated. Still further, it is appreciated that certain features of the invention which are, for clarity, described above and below in the context of separate embodiments, may also be provided in combination in a single embodiment. Conversely, various features of the invention that are, for brevity, described in context of a single embodiment, may also be provided separately or in any subcombination. Further, reference to values in ranges include each and every value within that range.

Example 1

This example illustrates the preparation of a ligand precursor compound having Formula II, where $R^2$ is $CF_3$, and $R^1$ and $R^3$ are H.

Preparation of
2,4-difluoro-3-trifluoromethylbenzeneboronic acid

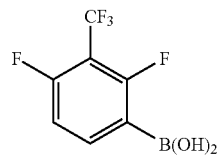

To a solution of 2.4 g of 2,6-difluoro-trifluoromethylbenzene in the mixture of 25 ml of dry ether and 25 ml of dry THF 7 ml of solution 2M butyl lithium in pentane was added dropwise at −70° C. The reaction mixture was stirred 15 min at −70° C. and 2 g of trimethylborate was added. The reaction was allowed to warm up to 25° C. and was diluted with 200 ml of 10% aqueous hydrochloric acid and extracted with ether (2×50 ml). The combined organic layers were washed with water (2×100 ml), dried over $MgSO_4$ and solvent was removed under vacuum at 50° C. to leave 3.4 g of crude boronic acid (containing ~50% of THF), which was used for the next reaction without further purification. $^1H$ NMR ($CDCl_3$): 6.9 (2H, t), 7.9 (1H, q), 5.3 (2H, br s); $^{19}F$ NMR: −56.68 (3F, t), −106.0 (1F, m), −108.0 (1F, m).

Preparation of
2(2,4-difluoro-3-trifluoromethylphenyl)-pyridine
Formula VIII

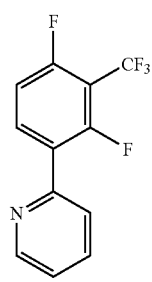

(VIII)

To a solution of 10 g potassium carbonate in 100 ml of degassed water, the solution of 3.4 g 2,4-difluoro-3-trifluoromethylbenzeneboronic acid (50% purity, the rest THF) in 50 ml of monoglyme was added, followed by the addition of 3.5 g of 2-bromopyridine, 0.1 g of dicyclohexyl(biphenyl)phosphine, 0.05 g of palladium acetate. The reaction mixture was refluxed (90-95° C.) for 16 h. The reaction mixture was diluted with 500 ml of water, extracted with dichloromethane (3×50 ml), the organic layer was washed with water (1×300 ml), dried over $MgSO_4$ and solvent was removed under vacuum. Crude product (3.2 g) was dissolved in 50 ml of hexane and the solution was passed through a short plug of silicagel (Silicagel 60, EM Science). The column was washed with another 30 ml of hexane. From the final solution, hexane was removed under vacuum to leave 1.6 g of slightly yellow liquid, which based on NMR analysis was 2-(2,4-difluoro-3-trifluoromethylphenyl)-pyridine, containing 27% of 2-bromopyridine. The crude material was used for the next reaction without further purification.

Example 2

This example illustrates the preparation of a complex having Formula XIII:

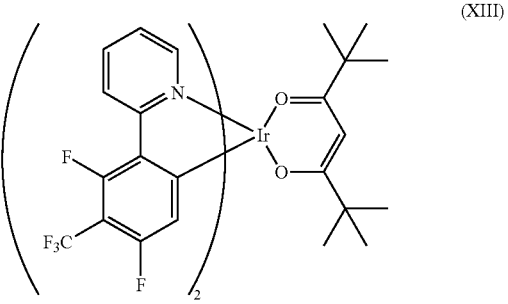

(XIII)

0.52 g of the precursor ligand from Example 1 was mixed with 0.38 g iridium chloride in 10 mL 2-ethoxyethanol and 1 mL water. This mixture was refluxed under nitrogen for 30 mins. The mixture was cooled, and to the cooled mixture was added 0.2 g di-t-butylacetylacetone (2,2,6,6-tetramethylheptanedione) and 300 mg sodium carbonate. Refluxing was continued for at least 30 mins. This was then cooled, evaporated to dryness in a nitrogen stream, extracted into methylene chloride, and filtered. The methylene chloride extract was dark orange in color and blue-green luminescent. The methylene chloride solution was then evaporated to dryness and chromatographed on silica to isolate the blue luminescent fraction. This fraction was then recrystallized from methylene chloride/methanol.

Analysis by NMR indicated the material to be the complex having Formula XIII.

Example 3

This example illustrates the preparation of the precursor phosphino-alcohol compound 1,1-bis(trifluoromethyl)-2-bis(triphenylphosphino)-ethanol ("PO-1H") for the ligand having Formula VII. The compound was made by two different methods.

a:

The phosphino alkanol was made according to the procedure in *Inorg. Chem.* (1985), 24 (22), pp. 3680-7. Under nitrogen, 1,1-bis(trifluoromethyl)ethylene oxide (12 g, 0.066 mol) was added dropwise to a pre-cooled (10-15° C.) solution of diphenylphosphine (10 g, 0.053 mol) in dry THF (50 mL). The reaction mixture was stirred at 25° C. for 2 days, after which NMR analysis indicated >90% conversion. The solvent was removed under vacuum and the residual viscous oil was distilled under vacuum to give 8 g of the fraction (b.p. 110-114° C. at 0.05 mm Hg) which crystallized on standing. Both the NMR data and m.p. (59-62° C.) of this material (>95% purity) were consistent with those reported in: Boere, R. T. et al., *Inorg. Chem.* (1985), 24, 3680. $^1$H NMR (CDCl$_3$, 20° C.), δ: 7.3-7.8 (m, 10H, arom. H); 2.8 (br. s.; 1H, OH); 2.2 (s, 2H, CH$_2$). $^{19}$F NMR (CDCl$_3$, 20° C.), δ: −77.3 (d, $J_{F-p}$ is 15.5 Hz). $^{31}$P NMR (CDCl$_3$, 20° C.), δ: −24.4 (septet, $J_{P-F}$ is 15.5 Hz).

Method b:

(i) Preparation of 1,1-bis(trifluoromethyl)-2-bromoethanol, BrCH$_2$C(CF$_3$)$_2$OH. 1,1-bis(trifluoromethyl)oxirane (100 g; 0.55 mol; prepared as described in WO 00/66575, 2000, to DuPont). was added slowly to 100 ml of 47% aqueous HBr placed in a round bottom glass flask equipped with a dry-ice condenser, thermometer, and magnetic stir bar at 30-40° C. The reaction mixture was stirred under reflux for 3 h. At that. point the temperature raised to 90° C. After cooling to room temperature, the bottom layer was separated, dried over MgSO$_4$, and distilled to give 104 g (72%) of BrCH$_2$C(CF$_3$)$_2$OH, b.p. 101-103° C. $^1$H NMR (CDCl$_3$): 3.50 (br s, 1H, —OH), 3.70 (s, 2H, CH$_2$). $^{19}$F NMR (CDCl$_3$): −75.9 (s). This material was dried over freshly calcined molecular sieves (4 Å) prior to the next step.

(ii) Under nitrogen, to a stirring solution of 1,1-bis(trifluoromethyl)-2-bromoethanol (5.64 g; prepared as described above) in dry ether (110 mL) cooled to −78° C., was added drop-wise 1.6 M n-BuLi in hexanes (Aldrich; 27 mL). After 1 h at −78° C., chlorodiphenylphosphine (Strem; 4.53 g) was added drop-wise, at vigorous stirring, to the resulting solution of the dilithiated derivative. After stirring the mixture for 3 h 20 min at −78° C., it was allowed to warm slowly to room temperature and then stirred at room temperature overnight. The solvents were removed under vacuum. Dichloromethane (10 mL) and trifluoroacetic acid (1.66 mL) were added to the residue, and the mixture was chromatographed on a silica gel column (5×25 cm) with dichloromethane. The product was isolated as an oil which crystallized upon drying under vacuum. The yield of the product as white crystalline solid was 5.3 g (71%). The compound was found identical with the material synthesized according to method a.

Example 4

This example illustrates the preparation of a complex having Formula XIV:

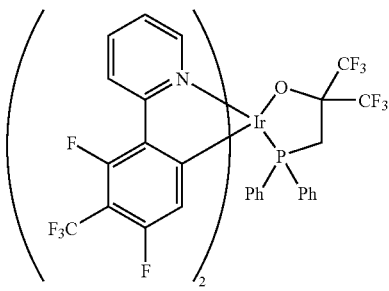

(XIV)

0.26 g Of the precursor ligand from Example 1 was mixed with 0.19 g iridium chloride in 10 mL 2-ethoxyethanol and 1 mL water. This mixture was refluxed under nitrogen for 30 mins. The mixture was cooled, and to the cooled mixture was added 0.37 g phosphinoalcohol (2 eq) from Example 3 and 300 mg sodium carbonate. Refluxing was continued for at least 30 mins. This was then cooled, evaporated to dryness in a nitrogen stream, extracted into methylene chloride, and filtered. The methylene chloride extract was light yellow in color and blue green luminescent. This solution was evaporated to dryness and chromatographed to isolate the blue luminescent fraction.

Analysis by TLC showed a very deep blue phosphorescent spot running at the solvent front and a turquoise phosphorescent spot running behind as the major fraction. A silica column with methylene chloride eluent was used to separate the two materials. Two fractions were collected: (i) a small amount of the fast running deeper blue material and (ii) a larger amount of pale yellow glassy material which was turquoise luminescent. Both of these materials were recrystallized from ethylacetate/hexanes to give pale crystals—blocks for the first material (i), and needles for the second material (ii). The major material (ii) was approximately 250 mg of fluffy pale yellow needles. Solutions of this material were sky blue photoluminescent. The solid was turquoise photoluminescent. Analysis by NMR indicated that this material had Formula XIV.

The second material was purified by additional chromatography using 50:50 hexanes:methylene chloride. A non-luminescent yellow band washed out ahead of the bright blue photoluminescent band. The blue photoluminescent band material was collected as a white solid (~25 mg). Analysis by NMR indicated that this material was a monocyclometallated hydrido material having Formula XV:

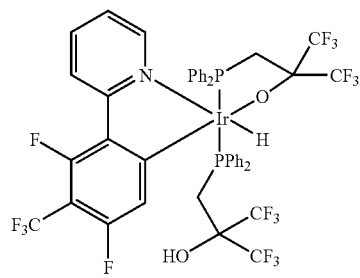

(XV)

Example 5

This example illustrates the preparation of bis-cyclometallated Ir 2-(2,4-difluorophenyl)-4-indolylpyridine complex —PO as the other ligand.

Example 5a

Preparation of the phenylpyridine ligand 2-(2,4-difluorophenyl)-4-indolylpyridine

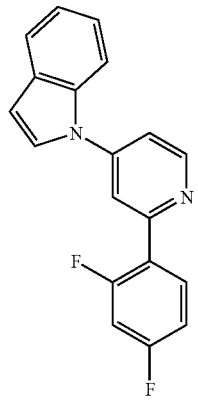

$C_{19}H_{12}F_2N_2$
Exact Mass: 306.10
Mol. Wt.: 306.31
C, 74.50; H, 3.95; F, 12.40; N, 9.15

44.9 mg (0.2 mmol) of palladium acetate, 70 mg (0.2 mmol) of 2-(dicyclohexylphosphino)biphenyl, 1.3455 grams (14 mmol) of sodium t-butoxide, 1.1281 grams (5 mmol) of 2-(2,4-difluorophenyl)-4-chloropyridine, and 0.7029 grams (6 mmol) of indole were mixed with 60 ml of toluene and refluxed for 48 hours. Next a double portion of the catalyst package and one more portion of indole was added to the mixture to reflux for 72 hours. The reaction contents were cooled to room temperature, diluted with dichloromethane and preabsorbed onto silica and chromatographed using methylene chloride eluent to isolate 0.978 grams of yellow solid in 63% yield.

Example 5b

Preparation of the bis cyclometallated iridium complex of 2-(2,4-difluorophenyl)-4-indolylpyridine 0.61 g of the phenylpyridine ligand from 5a above, 0.38 g iridium chloride in 10 mL 2-ethoxyethanol and 1 mL water were refluxed under nitrogen for 30 mins. The mixture was cooled and 0.2 g 2,4-pentanedionate (acac) and 300 mg sodium bicarbonate were added. The resulting mixture was refluxed for about 30 additional minutes. The progress of the reaction was checked by TLC, the mixture was then cooled and evaporated to dryness in a nitrogen stream. The product was extracted into methylene chloride and filtered. The methylene chloride solution was evaporated to dryness and chromatographed (checked with TLC) to isolate a blue luminescent fraction. The product was recrystallized from methylene chloride/methanol.

In this complex there are two phosphino alcohol ligands, one of which is bidentate and one of which is monodentate.

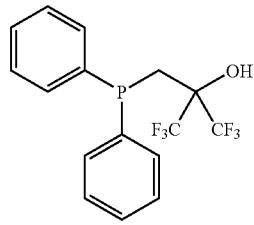

$C_{16}H_{13}F_6OP$
Exact Mass: 366.06
Mol. Wt.: 366.24
C, 52.47; H, 3.58; F, 31.12; O, 4.37; P, 8.46

The isolated product, an orange gum, was run down toluene/silica column. The fast running blue band which is the monocyclometallate was collected and then the slower running blue green band was collected by switching to methylene chloride eluent. The product was recrystallized in methylene chloride/methanol to yield yellow crystals which are turquoise luminescent.

The identity of the product was confirmed by $^1$H NMR.

Example 6

This example illustrates the preparation of tris-cyclometallated Ir 2-(2,4-difluoro-3-perfluoroisopropyl-phenyl)-4-phenyl(4-carbazoylphenyl)amino-pyridine complex.

Example 6a

Preparation of the ligand 2-(2,4-difluoro-3-perfluoroisopropyl-phenyl)-4-phenyl(4-carbazoylphenyl) amino-pyridine

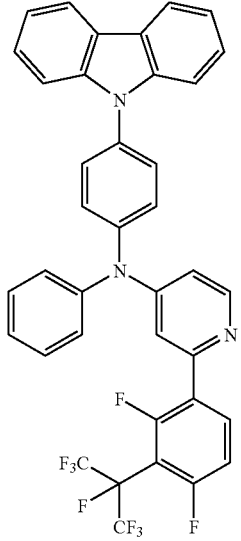

$C_{38}H_{22}F_9N_3$
Exact Mass: 691.17
Mol. Wt.: 691.59
C, 65.99; H, 3.21; F, 24.72; N, 6.08

2-(2,4-difluoro-3-perfluoroisopropylphenyl)-4-chloropyridine, (0.98 grams, 2.5 mmol), N-(4-phenylamino-phenyl)-carbazole (1.00 grams, 3.0 mmol), 30 mL toluene, palladium acetate (0.0224 grams, 0.1 mmol), 2-(dicyclohexylphosphino)biphenyl (0.0350 grams, 0.1 mmol) and sodium t-butoxide (0.6723 gram, 7.0 mmol) were combined in an inert atmosphere in a round bottomed flask equipped with magnetic stirring and a reflux condenser. The mixture was heated to 120° C. over 48 hrs under nitrogen and then cooled to room temperature. The solvent was evaporated and the mixture was purified by column chromatography to afford 1.04 grams of light brown solid, 60% yield whose identity was confirmed by 1-H nmr spectroscopy.

Example 6b

Preparation of the Tris-Cyclometallated Iridium Complex of Ligand from Example 6a 0.69 g Phenylpyridine ligand from example 6a above and 0.10 g iridium chloride were added to a 5 mL 2-ethoxyethanol and 1 mL water with 0.35 g silver trifluoroacetate. The mixture was stirred and refluxed under nitrogen for ~16 hr then cooled. The solution was evaporated to dryness by gentle heating in a nitrogen stream. The product was extracted into methylene chloride (large volume) and filtered through a silica plug. The residue was washed with additional methylene chloride until no further color eluted. The solution was evaporated to small volume then methanol was added to precipitate a product. The product was recrystallized (methanol/methylene chloride) and subjected to chromatography to purify.

The product gave a fast running green band on silica TLC using dichloromethane. A dirty yellow solid which is bright green luminescent was collected. This product was rerun down a silica column using toluene:hexane 50:50 eluent and a bright yellow band was collected and precipitated from toluene with hexane to give a lemon yellow solid which was blue green luminescent. $^1$H NMR was used to confirm identity.

Example 7

This example illustrates the preparation of bis-cyclometallated Ir 2-(2,4-difluoro-3-perfluoroisopropyl-phenyl)-4-carbazolyl-pyridine complex-2,2,6,6-tetramethylheptanedionate (t-butylacac) as the third ligand.

Example 7a

Preparation of the ligand 2-(2,4-difluoro-3-perfluoroisopropyl-phenyl)-4-carbazolyl-pyridine

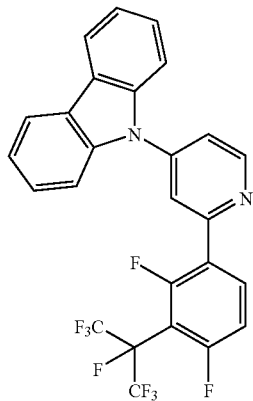

C$_{29}$H$_{13}$F$_9$N$_2$
Exact Mass: 524.09
Mol. Wt.: 524.38
C, 59.55; H, 2.50; F, 32.61; N, 5.34

Under an atmosphere of nitrogen a mixture of 2-(2,4-difluoro-3-perfluoroisopropyl-phenyl)-4-chloro-pyridine (1.1 g, 3.7 mmol), carbazole (0.68 g, 4 mmol), NaOtBu (0.53 g, 9.25 mmol), Pd$_2$(dba)$_3$ (0.100 g, 0.1 mmol) and P$^t$Bu$_3$ (0.07 g, 0.35 mmol) in toluene (30 mL) was heated to 100° C. for four days. The resulting mixture was diluted with methylene chloride and filtered through a plug of silica and celite. Upon evaporation of the solvent a dark brown viscous material was obtained which was purified by washing with hexanes to form a light brown precipitate, then chromatography on silica (5% EtOAC/hexanes) to yield the desired product as a yellow oil (0.800 g, 55%). $^1$H and $^{19}$F NMR confirmed the product identity.

Example 7b

Preparation of the Bis-Cyclometallated Iridium Complex of the Ligand Prepared in Example 7a 0.20 g of phenylpyridine ligand prepared in example 7a and 0.08 g iridium chloride in 10 mL 2-ethoxyethanol and 1 mL water were added to a reaction vessel. The mixture was refluxed under nitrogen for 30 mins. The mixture was cooled and then 0.1 g t-butylacac and 100 mg sodium bicarbonate were added to the mixture. The mixture was refluxed for an additional 30 minutes. The progress of the reaction was checked by TLC. The reaction was then cooled and evaporated to dryness in a nitrogen stream. The product was extracted into methylene chloride and filtered. The resulting solution was evaporated to dryness and chromatographed (checking with TLC) to isolate a blue luminescent fraction. $^1$H NMR confirmed the identity of the product. The product was recrystallized from methylene chloride/methanol.

The dark orange gum collected after evaporation of the 2-ethoxyethanol solvent was subjected to TLC which showed a fast running (toluene) greenish luminescent band. The material was chromatographed on silica using toluene eluent to collect. A yellow solid which is greenish luminescent (turquoise) was isolated. $^1$H NMR confirmed the product identity.

Example 8

This example illustrates the preparation of tris-cyclometallated Ir 2-(2,4-difluoro-phenyl)-4-carbazole-pyridine complex.

0.36 g of phenylpyridine ligand (shown below) and 0.13 g iridium chloride with 0.25 g silver trifluoroacetate into 5 mL 2-ethoxyethanol and 0.5 mL water was added to a reaction vessel. The mixture was stirred and refluxed under nitrogen for ~1 hr and then cooled. The solution was evaporated to dryness by gentle heating in a nitrogen stream.

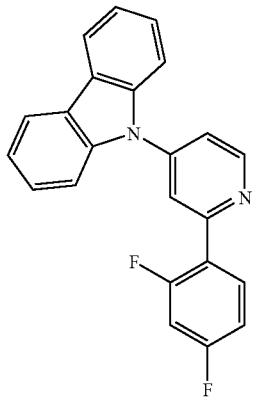

$C_{23}H_{14}F_2N_2$
Exact Mass: 356.11
Mol. Wt.: 356.37
C, 77.52; H, 3.96; F, 10.66; N, 7.86

The reaction mixture was extracted with methylene chloride which was run down a silica column, eluting with toluene. A bright yellow band was collected. The material was blue green luminescent. The solution was evaporated in nitrogen over weekend and then run down a basic alumina column eluting with methylene chloride. A bright blue green luminescent material was collected as a yellow solution. The product was evaporated to dryness and washed with hexanes then filtered to collect 100 mg of yellow solid which is green luminescent. Product identity was confirmed by $^1$H NMR.

What is claimed is:

1. A complex having Formula I

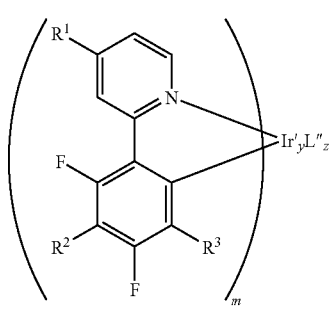

(I)

wherein:
R$^1$ is indole, indoline, carbazole, tetrahydrocarbazole, phenanthroline, phenazine, phenanthridine, quinoxaline, pyrrole, azole, oxazole, or pyridine, each of which is attached via nitrogen; or R$^1$ is CHAr$_2$;
R$^2$ is H, $C_nF_{2n+1}$, $C_nF_{2n+1}SO_2$, COOR$^4$, or CN;
R$^3$ is H, $C_nF_{2n+1}$, $C_nF_{2n+1}SO_2$, COOR$^4$, or CN;
R$^4$ is the same or different at each occurrence and is H, alkyl, or aryl;
each Ar is independently an aryl group;
L' is a polydentate ligand that is not a phenylpyridine, phenylpyrimidine, or phenylquinoline;
L" is a monodentate ligand, and is not a phenylpyridine, phenylpyrimidine, or phenylquinoline;
m is 1, 2 or 3;
n is an integer from 1 through 20;
y is 0, 1 or 2; and
z is 0 or an integer from 1 through 4, with the proviso that the compound is charge neutral and the iridium is hexa-coordinate.

2. The complex of claim 1 wherein R$^2$ and R$^3$ are independently selected from H, CF$_3$, C$_2$F$_3$, n-C$_3$F$_7$, i-C$_3$F$_7$, C$_4$F$_9$, CF$_3$SO$_2$, COOR$^4$ and CN.

3. The complex of claim 1 wherein R$^4$ is phenyl.

4. The complex of claim 1 wherein m is 3, y is 0, and z is 0.

5. The complex of claim 1 wherein m is 2, y is 1, z is 0, and L' is a monoanionic bidentate ligand.

6. The complex of claim 2 wherein L' has a coordinating group selected from amino, imino, amido, alkoxide, carboxylate, phosphino, and thiolate.

7. The complex of claim 5 wherein L' is selected from β-enolate ligands, N-analogs of β-enolate ligands, S-analogs of β-enolate ligands, aminocarboxylate ligands, iminocarboxylate ligands, salicylate ligands, hydroxyquinolinate ligands, S-analogs of hydroxyquinolinate ligands, phosphinoalkoxide ligands, and a ligand coordinated through a carbon atom that is part of an aromatic group.

8. The complex of claim 6 wherein L' has Formula VII:

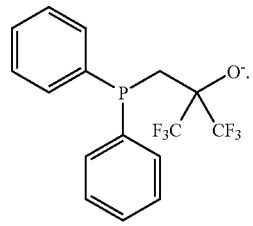

(VII)

9. The complex of claim 1 wherein m is 1, y is 1, and z is 2.

10. The complex of claim 9 wherein at least one L" is a hydride.

11. A compound of the formula:

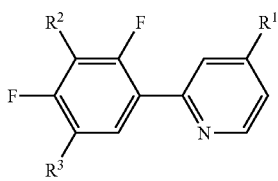

(II)

wherein:
R$^1$ is CHAr$_2$;
R$^2$ is H, $C_nF_{2n+1}$, $C_nF_{2n+1}SO_2$, COOR$^4$, or CN;
R$^3$ is H, $C_nF_{2n+1}$, $C_nF_{2n+1}SO_2$, COOR$^4$, or CN;
wherein each R$^4$ is the same or different at each occurrence and is H, alkyl, or aryl; and
each Ar is independently an aryl group.

12. An organic electronic device having at least one complex of claim 1.

13. An article useful in the manufacture of an organic electronic device comprising at least one layer comprising at least one complex of claim 1.

14. A composition comprising at least one complex of claim 1.

15. The composition of claim 14 further comprising at least one of solvent, processing aid, charge transporting material, and charge blocking material.

* * * * *